US008724772B2

(12) United States Patent
Nishii (10) Patent No.: US 8,724,772 B2
(45) Date of Patent: May 13, 2014

(54) X-RAY FLUOROSCOPIC RADIOGRAPHING APPARATUS AND METHOD (75) Inventor: Yuichi Nishii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 290 days.

(21) Appl. No.: 13/293,218

(22) Filed: Nov. 10, 2011

(65) Prior Publication Data

US 2012/0128129 A1 May 24, 2012

(30) Foreign Application Priority Data

Nov. 24, 2010 (JP) ................................ 2010-260965

(51) Int. Cl.
*A61B 6/02* (2006.01)
(52) U.S. Cl.
USPC .............................. 378/42; 378/98
(58) Field of Classification Search
USPC ................. 378/42, 62, 98; 382/128, 130, 132
See application file for complete search history.

(56) References Cited

U.S. PATENT DOCUMENTS

| 4,394,684 | A | 7/1983 | Verhoeven | 378/98.12 |
|---|---|---|---|---|
| 6,204,878 | B1 | 3/2001 | Hieda | 348/240.99 |
| 2008/0253679 | A1 | 10/2008 | Takahashi | 382/261 |
| 2009/0052753 | A1* | 2/2009 | Sugahara | 382/128 |
| 2009/0292181 | A1* | 11/2009 | Donaldson | 600/301 |
| 2011/0052016 | A1 | 3/2011 | Nishii | 382/128 |

FOREIGN PATENT DOCUMENTS

| CN | 1111866 | 11/1995 |
|---|---|---|
| JP | 2003-185600 | 7/2003 |
| JP | 2007-071735 | 3/2007 |
| JP | 2007-159913 | 6/2007 |
| JP | 2008-219654 | 9/2008 |

OTHER PUBLICATIONS

Office Action issued on Dec. 23, 2013, in counterpart Chinese (P.R. C.) patent application 201110382200.4, with translation.

* cited by examiner

*Primary Examiner* — Hoon Song
(74) *Attorney, Agent, or Firm* — Fitzpatrick, Cella, Harper & Scinto

(57) ABSTRACT

An X-ray fluoroscopic radiographing apparatus comprises a display unit that processes a received X-ray moving image and instantaneously displays the moving image; a storing unit that stores the received moving image as a non-processed raw image; an instructing unit that instructs the raw image to be referred to from the stored raw images; a second display unit that processes the instructed raw image and displays the processed raw image; a changing unit that changes the image process in the second display unit; a second storing unit that stores image process information obtained by the changing unit in association with the instructed raw image; a second instructing unit that instructs the raw image to be transferred from the stored raw images; and a transferring unit that executes the image process associated by the second storing unit to the instructed raw image and transfers the processed raw image to a destination.

8 Claims, 8 Drawing Sheets

Out(n)=(1-a)*In(n)+a*Out(n-1)

X-RAY FLUOROSCOPIC RADIOGRAPHING APPARATUS AND METHOD

BACKGROUND OF THE INVENTION

1. Field of the Invention

The present invention relates to an X-ray fluoroscopic radiographing apparatus and a method which can instruct an optimum image process at the time of reference or transfer.

2. Description of the Related Art

An X-ray fluoroscopic radiographing apparatus for performing a fluoroscopic radiographing in a real-time manner for the purpose of IVR (Interventional Radiology) or the like is constructed by an X-ray image pickup apparatus and a display control apparatus. In an X-ray image pickup apparatus in the related art, analog data is transferred to a display control apparatus via a video signal by using an analog image pickup tube or a CCD coupled with an image intensifier and an image is displayed to a CRT monitor or the like in an analog manner. In recent years, digitalization has progressed and a flat panel sensor (FPD) has been substituted by the image intensifier (+analog image pickup tube or CCD). The CRT monitor has also been substituted by a high precision liquid crystal monitor via a DVI (Digital Visual Interface).

In this manner, a full digital system which can perform operations from the radiographing to the display is being constructed. Generally, an image process (recursive process) for synthesizing an image in a time base direction is executed to a moving image radiographed in such an apparatus for the purpose of noise suppression. For example, there is a disclosure regarding the recursive process in Japanese Patent Application Laid-Open No. 2008-219654.

With respect to a moving image which was fluoroscopically radiographed by the X-ray fluoroscopic radiographing apparatus, processing contents of an image process such as a recursive process or the like can be changed before or during the fluoroscopic radiographing. However, in the apparatus in the related art, only the processed image to which the recursive process or the like has already been executed is stored. Therefore, such operations that the image before the image process is obtained, the processing contents of the image process are adjusted, and the image process is executed cannot be performed. However, there is such a demand that the user wants to enable the recursive process to be adjusted in order to improve a diagnosis ability even after the fluoroscopic radiographing or the user wants to adjust the image process at each of the time of reference and the time of image transfer. For example, there is such a demand that at the time of reference, even if an after-image was left, the user wants to refer to the noise-suppressed image. On the other hand, in the case of a film output, there is such a demand that even if noises of a certain extent are permitted, the user wants to suppress the after-image.

SUMMARY OF THE INVENTION

The present invention has been made in consideration of the above situation, and has as its object to obtain an image in which a user-desired image process has been executed to a raw image obtained from an X-ray image radiographing apparatus.

In order to achieve the object, the invention provides with an X-ray fluoroscopic radiographing apparatus comprising: an instantaneous display unit that processes a received X-ray moving image and instantaneously displays the processed moving image; a raw image storing unit that stores the received X-ray moving image as a non-processed raw image; a reference image instructing unit that instructs the raw image to be referred to from the raw images stored by the raw image storing unit; a reference image display unit that processes the raw image instructed by the reference image instructing unit and displays the processed raw image; an image process changing unit that changes the image process in the reference image display unit; an image process information storing unit that stores image process information obtained by the change by the image process changing unit in association with the instructed raw image; a transfer image instructing unit that instructs the raw image to be transferred from the stored raw images; and an image transferring unit that executes the image process associated by the image process information storing unit to the raw image instructed by the transfer image instructing unit and transfers the processed raw image to a transfer destination.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Preferred embodiments of the present invention will be described in detail in accordance with the accompanying drawings.

Embodiment 1

Figure 1:
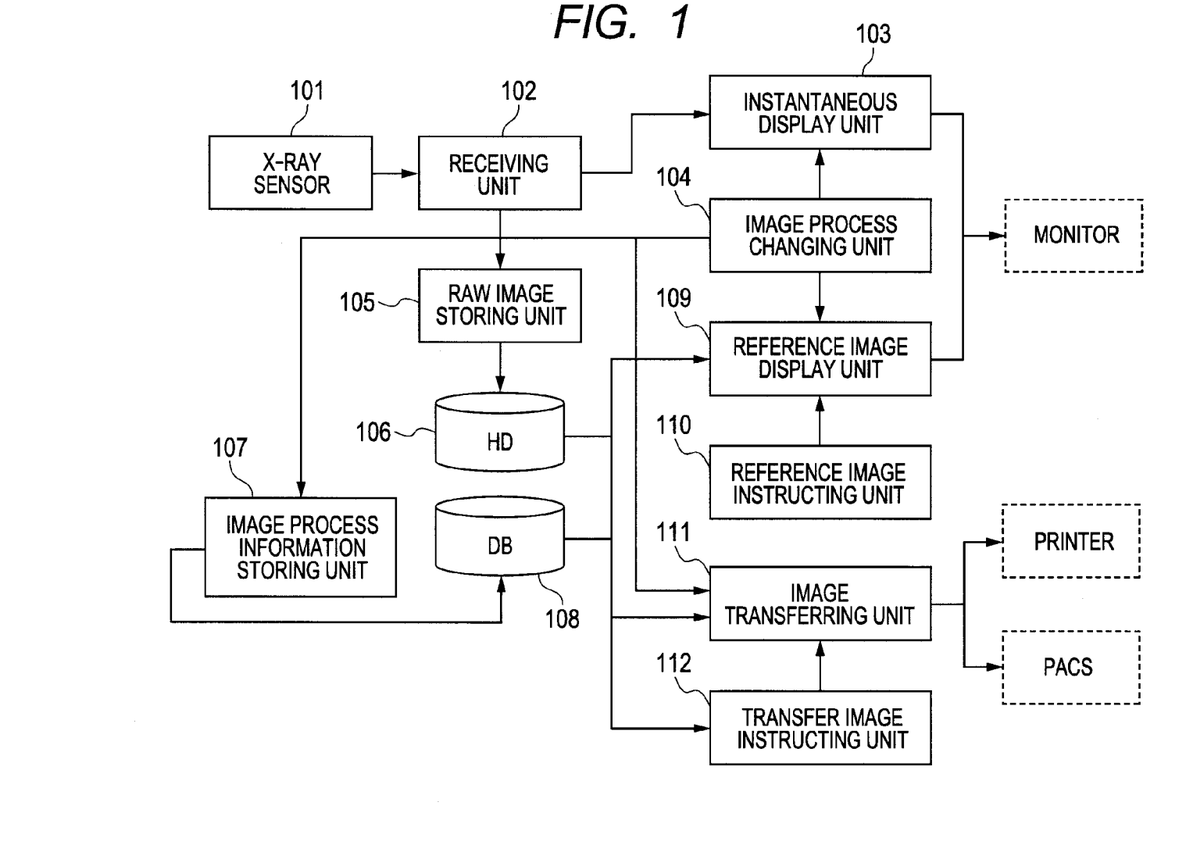
FIG. 1 is a diagram illustrating a schematic construction of an X-ray fluoroscopic radiographing apparatus in an embodiment of the invention.
Figure 11:
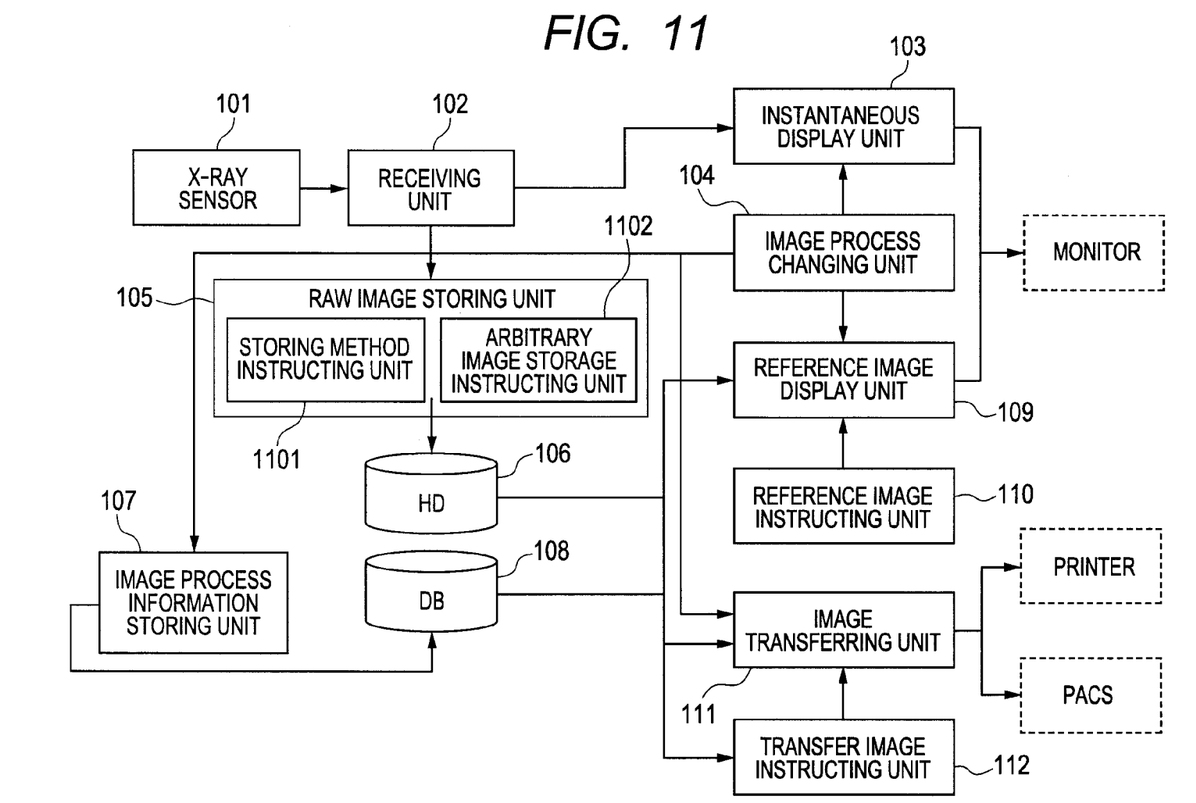
FIG. 11 is a diagram illustrating another schematic construction of the X-ray fluoroscopic radiographing apparatus in the embodiment of the invention.

FIGS. 1 and 11 are block diagrams each illustrating a construction of an X-ray fluoroscopic radiographing apparatus according to the embodiment.

Figure 2:
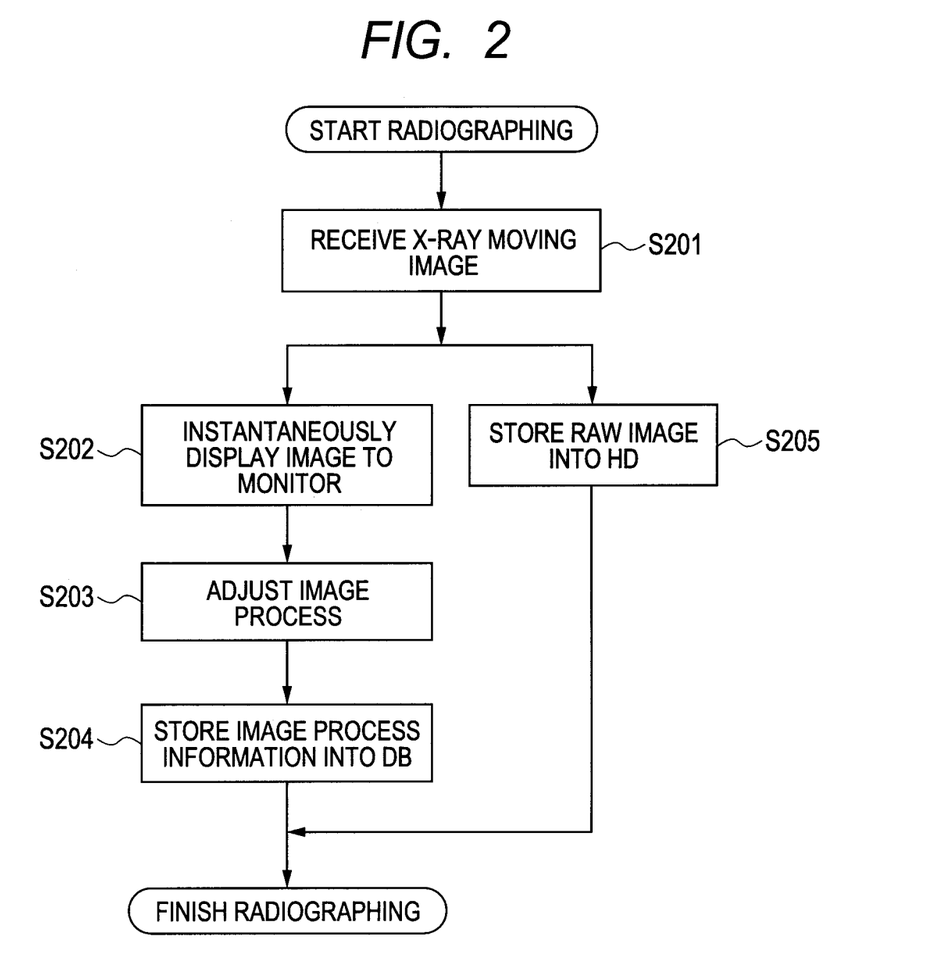
FIG. 2 is a flowchart illustrating a sequence in the case of radiographing in a setting of instantaneously storing.

First, a flow of a radiographing in the case where a mode in which an image is instantaneously stored has previously been set by a storing method instructing unit 1101 (FIG. 11) will be described with reference to a sequence of FIG. 2. An X-ray moving image transmitted from an X-ray sensor 101 is received (S201) by a receiving unit 102. An image process is executed by an instantaneous display unit 103 and a processed image is displayed to a monitor (S202). At this time, the image process can be adjusted (S203) in an image process changing unit 104. Image process information obtained by the adjustment by the image process changing unit 104 is stored (S204) into a database (hereinbelow, abbreviated to "DB") 108 by an image process information storing unit 107. A raw image which was received by the receiving unit 102 and is not subjected to the image process is stored (S205) into a hard disk (hereinbelow, abbreviated to "HD") 106 by a raw image storing unit 105. At this time, the image process information and the raw image are stored in association with each other.

Figure 3:
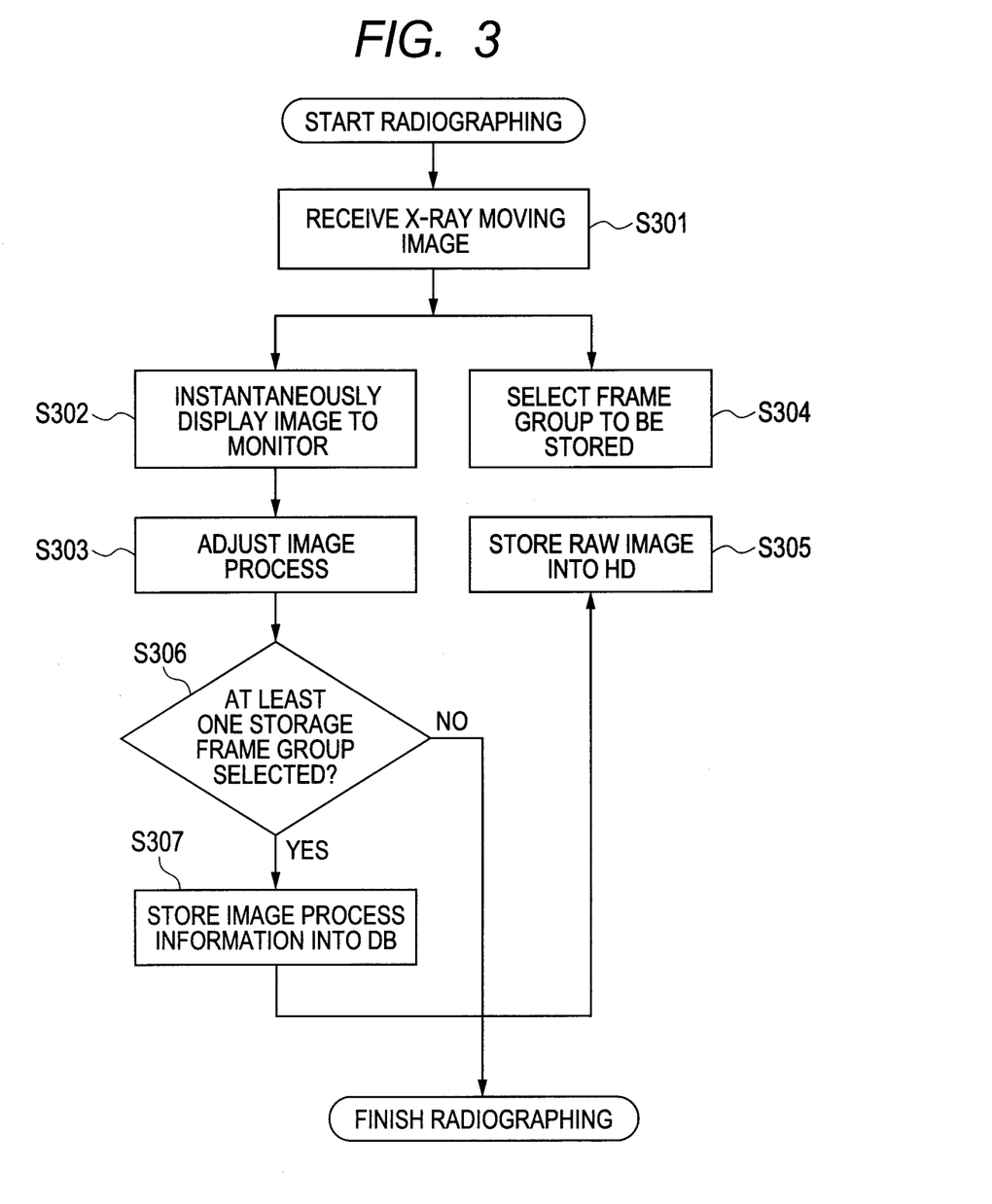
FIG. 3 is a flowchart illustrating a sequence in the case of radiographing in a mode of selecting a frame which is stored later.

Subsequently, a flow of a radiographing in the case where a mode in which after the radiographing, an image is selected and stored has previously been set by the storing method instructing unit 1101 will be described with reference to a sequence of FIG. 3. The X-ray moving image transmitted from the X-ray sensor 101 is received (S301) by the receiving unit 102. The image process is executed by the instantaneous display unit 103 and the processed image is displayed to the monitor (S302). At this time, the image process can be adjusted (S303) in the image process changing unit 104. After the reception, a frame group to be stored is selected from the received frame groups by an arbitrary image storage instructing unit 1102 (S304) and stored into the HD 106 (S305) by the raw image storing unit 105. If at least one frame group was selected (S306) by the arbitrary image storage instructing unit 1102, the image process information is stored into the DB 108 (S307) by the image process information storing unit 107. At this time, the image process information and the raw image are stored in association with each other.

Figure 4:
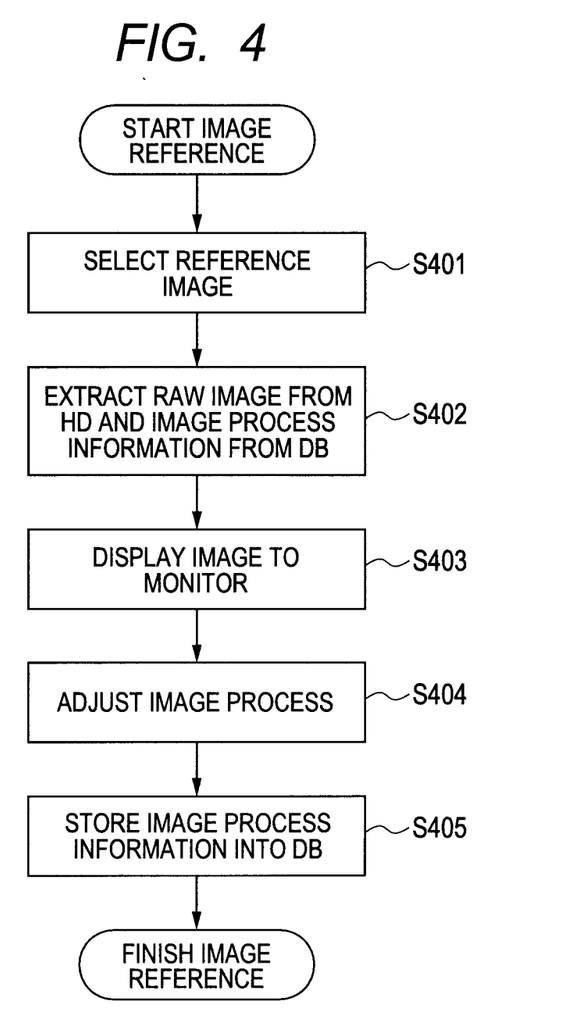
FIG. 4 is a flowchart illustrating a sequence at the time of image reference.

A flow in the case of referring to the image stored by one of the above two kinds of storing methods will be described with reference to a sequence of FIG. 4. When the image selecting instruction (S401) is issued by a reference image instructing unit 110, a reference image display unit 109 extracts the raw image corresponding to the selecting instruction from the HD 106, extracts the image process information from the DB 108 (S402), executes the image process to the raw image, and displays the processed image to the monitor (S403). At this time, the image process can be adjusted (S404) in the image process changing unit 104. The image process information obtained by the adjustment by the image process changing unit 104 is stored into the DB 108 (S405) by the image process information storing unit 107.

Figure 5:
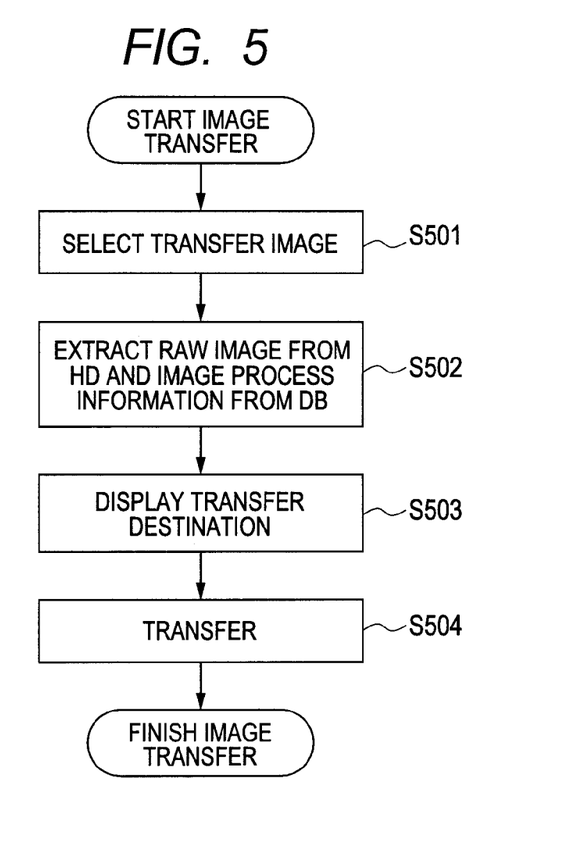
FIG. 5 is a flowchart illustrating a sequence at the time of image transfer.

A flow in the case of transferring the image stored by one of the above two kinds of storing methods will be described with reference to a sequence of FIG. 5. In response to the image selecting instruction (S501) by a transfer image instructing unit 112, an image transferring unit 111 extracts the corresponding raw image from the HD 106, extracts the image process information from the DB 108 (S502), executes the image process to the raw image, instructs a transfer destination (S503), and transfers (S504). As a transfer destination, an image storage communication system PACS (Picture Archiving and Communication System) which is used in a medical treatment, a printer, another system, or the like is presumed.

In the constructions illustrated in FIGS. 1 and 11, the apparatus has one image process changing unit 104 and can individually change (adjust) the image process in the instantaneous display unit 103, reference image display unit 109, and image transferring unit 111. Further, in the above construction, the apparatus has one image process information storing unit 107 and can individually store the image process information obtained by the above individual change (adjustment) by the image process changing unit 104. Besides the instantaneous display unit 103, the image process changing unit 104 and the image process information storing unit 107 may be provided for the reference image display unit 109 and the image transferring unit 111, respectively, and the image can be referred to or transferred by using a plurality of image process information.

By the above construction, such a selective use that at the time of reference, the image in which the noises are suppressed is referred to although an after-image remains, and at the time of film output, the image in which the noises of a certain extent are permitted and the after-image is suppressed is output can be performed. If there are a plurality of transfer destinations, the image process changing unit 104 and the image process information storing unit 107 may be provided in correspondence to each of the transfer destinations, a change (adjustment) of the image process corresponding to the transfer destination is performed, and the image can be transferred by using the image process information obtained by the change.

Figure 6:
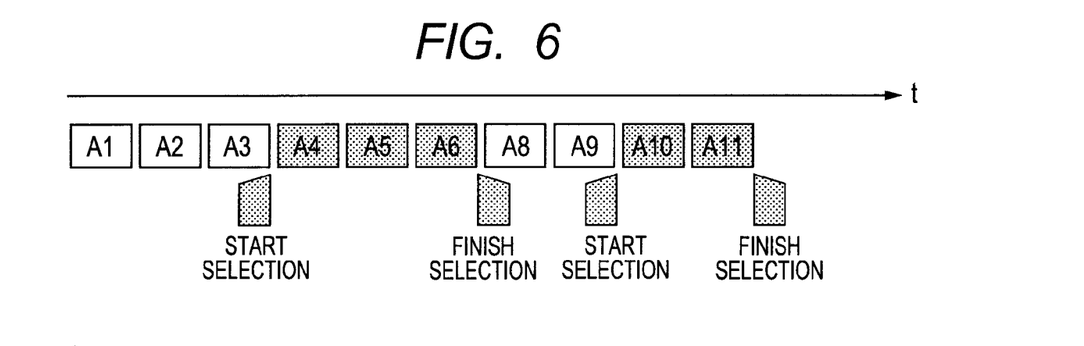
FIG. 6 is a diagram illustrating an example of image instructions of a reference image instructing unit and a transfer image instructing unit.
Figure 7:
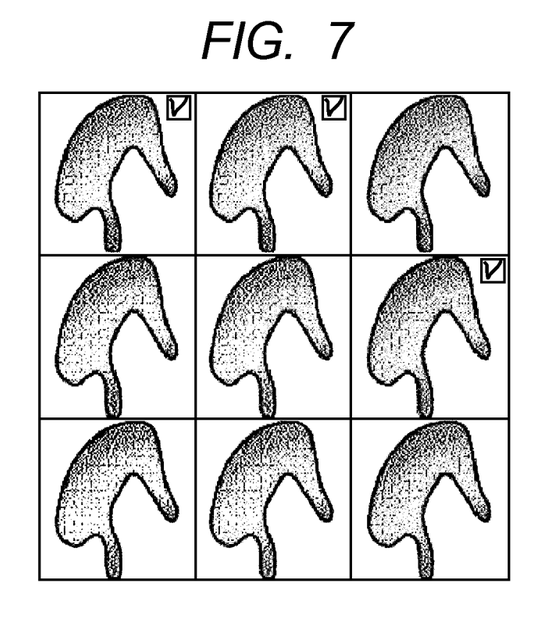
FIG. 7 is a diagram illustrating another example of image instructions of the reference image instructing unit and the transfer image instructing unit.
Figure 8:
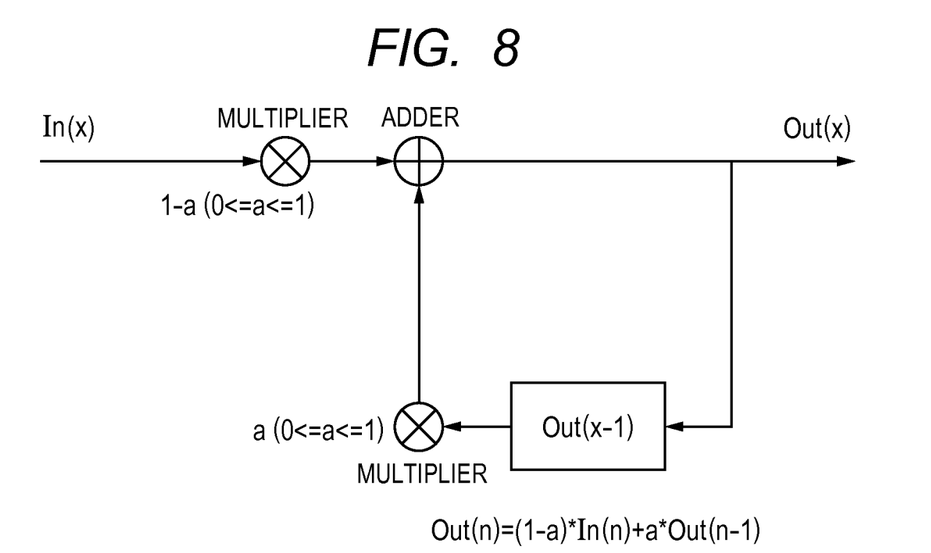
FIG. 8 is a diagram illustrating contents of a recursive process.

In the reference image instructing unit 110 and the transfer image instructing unit 112, a method of instructing start and end positions of frames which are selected on a time line as illustrated in FIG. 6, a method of instructing the reference/transfer every frame as illustrated in FIG. 7, or the like is considered. The instructing units are not limited to those methods.

Embodiment 2

An image process (recursive process) for synthesizing an image in a time base direction as one of the image processes which are changed (adjusted) in the image process changing unit 104 will be described. The recursive process is such an image process that a coefficient a is multiplied to an input frame In(x) and a one-precedent frame output Out(x−1) and obtained outputs are recursively added.

In the case where the raw image is stored like an invention, in order to reproduce the image at the time of the instantaneous display by performing the recursive process, if all frames precedent to an arbitrary frame are not added, such an image cannot be reproduced. However, the larger a frame number difference is, the smaller an influence of the precedent frames is although it depends on a weight of the coefficient a. Therefore, in the invention, it is assumed that it is sufficient to add the frames from the N-precedent frame. However, when an arbitrary frame number is less than N, since the number of images is inherently small, it is sufficient to add the existing frames. If the recursive-processed frames exist within N frames from the arbitrary frame, it is sufficient to recursive-process only the frames corresponding to the difference from the relevant frame.

That is, in a designated arbitrary frame group;

(1) If no recursive-processed frames exist within N frames before the present frame and the number of the present frame is less than N, the recursive process is executed to the frames within a range from the head frame to the present frame.

(2) If no recursive-processed frames exist within N frames before the present frame and the number of the present frame is equal to or larger than N, the recursive process is executed to the frames within a range from the N-precedent frame of the present frame to the present frame.

(3) If recursive-processed frames exist within (N−1) frames before the present frame, the relevant frame is set to an initial image and the recursive process is executed to the frames within a range from the frame next to the relevant frame to the present frame.

Figure 9:
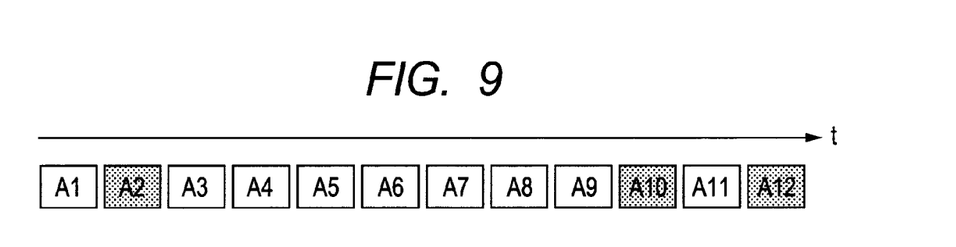
FIG. 9 is a diagram illustrating an example of the recursive process.

Examples in the above cases (1) to (3) will now be described. It is assumed that images A1 to A12 were radiographed and stored as illustrated in FIG. 9. It is assumed that the images A2, A10, and A12 were selected and, further, N=4.

(I) The image A2 corresponds to the above case (1) and the recursive-processed image of A2 is formed by recursive-processing the images A1 and A2.

(II) The image A10 corresponds to the above case (2) and the recursive-processed image of A10 is formed by recursive-processing the images by using A6 to A10.

(III) The image A12 corresponds to the above case (3) and since the image A10 has already existed, the recursive-processed image of A12 is formed by recursive-processing the images A11 and A12 on the basis of the recursive-processed image of A10.

At this time, as management information of the frames, the images are managed as follows:

(a) unnecessary image (S);

(b) image which is recursive-processed but is not output (I); or (c) image which is recursive-processed and is output (O).

Figure 10:
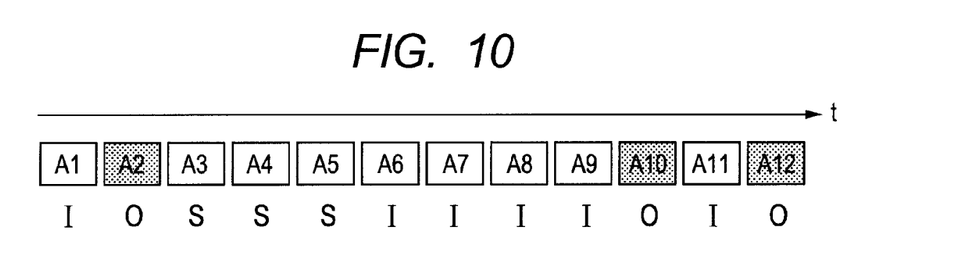
FIG. 10 is a diagram illustrating a frame management system in the recursive process in FIG. 9.

In the above examples, the images A1 to A12 are managed as illustrated in FIG. 10. Although a method of previously storing all images in order to perform the recursive process as mentioned above may be used, actually, since the frames necessary for the selected frames are only the images of I and O excluding the images of S, a method of storing only the images of I and O at the stage of storing can be also used.

In accordance with the above classification, the reference image display unit 109 or the image transferring unit 111 executes processes as follows to the arbitrary frame group designated by the reference image instructing unit 110 or the transfer image instructing unit 112.

(1) If no recursive-processed frames exist within N frames before the present frame and the number of the present frame is less than N, the recursive process is executed to the frames within a range from the head frame to the present frame.

(2) If no recursive-processed frames exist within N frames before the present frame and the number of the present frame is equal to or larger than N, the recursive process is executed to the frames within a range from the N-precedent frame of the present frame to the present frame.

(3) If recursive-processed frames exist within (N−1) frames before the present frame, the present frame is set to an initial image and the recursive process is executed to the frames within a range from the frame next to the relevant frame to the present frame.

In accordance with the above classification, the raw image storing unit 105 executes processes as follows to the arbitrary frame group designated by the arbitrary image storage instructing unit 1102.

(1) If no recursive-processed frames exist within N frames before the present frame and the number of the present frame is less than N, the frames within a range from the head frame to the present frame are stored.

(2) If no recursive-processed frames exist within N frames before the present frame and the number of the present frame is equal to or larger than N, the frames within a range from the N-precedent frame of the present frame to the present frame are stored.

(3) If recursive-processed frames exist within (N−1) frames before the present frame, the frames within a range from the frame next to the relevant frame to the present frame are stored.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-260965, filed Nov. 24, 2010, which is hereby incorporated by reference herein in its entirety.

What is claimed is:

1. An X-ray fluoroscopic radiographing apparatus comprising:

an instantaneous display unit configured to process a received X-ray moving image and instantaneously display the processed moving image;

a raw image storing unit configured to store the received X-ray moving image as a non-processed raw image;

a reference image instructing unit configured to instruct the raw image to be referred to from the raw images stored by the raw image storing unit;

a reference image display unit configured to process the raw image instructed by the reference image instructing unit and display the processed raw image;

an image process changing unit configured to change the image process in the reference image display unit;

an image process information storing unit configured to store image process information obtained by the change by the image process changing unit in association with the instructed raw image;

a transfer image instructing unit configured to instruct the raw image to be transferred from the stored raw images; and an image transferring unit configured to execute the image process associated by the image process information storing unit to the raw image instructed by the transfer image instructing unit and transfer the processed raw image to a transfer destination.

2. An apparatus according to claim 1, wherein the image transferring unit can transfer the raw image to a plurality of transfer destinations and the image process changing unit can individually change the image process in correspondence to each of the plurality of transfer destinations.

3. An apparatus according to claim 1, wherein the image process is a recursive process and the reference image display unit or the image transferring unit executes the recursive process to frames of the raw image instructed by the reference image instructing unit or the transfer image instructing unit in such a manner that:

if no recursive-processed frames exist within N frames before a present frame and the number of the present frame is less than N, the recursive process is executed to the frames within a range from a head frame to the present frame;

if no recursive-processed frames exist within N frames before the present frame and the number of the present frame is equal to or larger than N, the recursive process is executed to the frames within a range from the N-precedent frame of the present frame to the present frame; and if recursive-processed frames exist within the (N−1) frames before the present frame, the relevant frame is set to an initial image and the recursive process is executed to the frames within a range from the frame next to the relevant frame to the present frame.

4. An apparatus according to claim 1, wherein the raw image storing unit further has a storing method instructing unit configured to instruct either a mode in which the received X-ray moving image is instantaneously stored or a mode in which it is stored later, and if the mode of instantaneously storing the image is instructed by the storing method instructing unit, the X-ray moving image is instantaneously stored, and if the mode of storing the image later is instructed by the storing method instructing unit, an arbitrary frame group of the X-ray moving image is selected and stored as a raw image.

5. An apparatus according to claim 4, wherein the image process is a recursive process and the raw image storing unit stores frames in the selected arbitrary frame group in such a manner that:

if no recursive-processed frames exist within N frames before a present frame and the number of the present frame is less than N, the frames within a range from a head frame to the present frame are stored;

if no recursive-processed frames exist within N frames before the present frame and the number of the present frame is equal to or larger than N, the frames within a range from the N-precedent frame of the present frame to the present frame are stored; and if recursive-processed frames exist within (N−1) frames before the present frame, the frames within a range from the frame next to the relevant frame to the present frame are stored.

6. An apparatus according to claim 4, wherein the raw image storing unit stores all images obtained by the same radiographing as that performed to the selected arbitrary frame group.

7. An X-ray fluoroscopic radiographing method comprising:

an instantaneous display step of processing a received X-ray moving image and instantaneously displaying the processed moving image;

a raw image storing step of storing the received X-ray moving image as a non-processed raw image;

a reference image instructing step of instructing the raw image to be referred to from the raw images stored in the raw image storing step;

a reference image display step of processing the raw image instructed in the reference image instructing step and displaying the processed raw image;

an image process changing step of changing the image process in the reference image display step;

an image process information storing step of storing image process information obtained by the change in the image process changing step in association with the instructed raw image;

a transfer image instructing step of instructing the raw image to be transferred from the stored raw images; and an image transferring step of executing the image process associated in the image process information storing step to the raw image instructed in the transfer image instructing step and transferring the processed raw image to a transfer destination.

8. A non-transitory computer-readable storage medium storing a computer program that causes a computer to execute the X-ray fluoroscopic radiographing method according to claim 7.

* * * * *